US012644096B2

(12) United States Patent
Oddone et al.

(10) Patent No.: US 12,644,096 B2
(45) Date of Patent: Jun. 2, 2026

(54) METHOD FOR INCREASING ROMIDEPSIN PRODUCTION FROM FERMENTATION BROTH

(71) Applicant: Pro Farm Group, Inc., Davis, CA (US)

(72) Inventors: Gian Oddone, Davis, CA (US); Jacob Blodgett, Davis, CA (US); Raul Reveles, Davis, CA (US)

(73) Assignee: PRO FARM GROUP, INC., Davis, CA (US)

( * ) Notice: Subject to any disclaimer, the term of this patent is extended or adjusted under 35 U.S.C. 154(b) by 378 days.

(21) Appl. No.: 17/413,179

(22) PCT Filed: Oct. 29, 2019

(86) PCT No.: PCT/US2019/058493

§ 371 (c)(1),
(2) Date: Jun. 11, 2021

(87) PCT Pub. No.: WO2020/139453

PCT Pub. Date: Jul. 2, 2020

(65) Prior Publication Data

US 2022/0049213 A1 Feb. 17, 2022

Related U.S. Application Data

(60) Provisional application No. 62/904,124, filed on Sep. 23, 2019, provisional application No. 62/784,656, filed on Dec. 24, 2018.

(51) Int. Cl.
*C12N 1/38* (2006.01)
*C07K 5/103* (2006.01)
*C12N 1/20* (2026.01)

(52) U.S. Cl.
CPC ................ *C12N 1/38* (2013.01); *C07K 5/101* (2013.01); *C12N 1/20* (2013.01)

(58) Field of Classification Search
CPC ............. C12N 1/38; C12N 1/20; C07K 5/101
See application file for complete search history.

(56) References Cited

U.S. PATENT DOCUMENTS

| | | | | |
|---|---|---|---|---|
| 8,426,556 B2 * | 4/2013 | Ueda | A61K 9/00 530/317 |
| 8,691,534 B2 | 4/2014 | Verdine et al. | |
| 9,624,271 B2 | 4/2017 | Hanko et al. | |
| 2013/0236928 A1 | 9/2013 | Vrolijk et al. | |
| 2014/0221207 A1 * | 8/2014 | Asolkar | A01N 63/02 |
| 2015/0010899 A1 | 1/2015 | Riisgaard et al. | |

OTHER PUBLICATIONS

Slyter, L. L., & Wolin, M. J. (1967). Copper sulfate-induced fermentation changes in continuous cultures of the rumen microbial ecosystem. Applied microbiology, 15(5), 1160-1164. (Year: 1967).*

VanderMolen, K. M., McCulloch, W., Pearce, C. J., & Oberlies, N. H. (2011). Romidepsin (Istodax, NSC 630176, FR901228, FK228, depsipeptide): a natural product recently approved for cutaneous T-cell lymphoma. The Journal of antibiotics, 64(8), 525-531. (Year: 2011).*

Saraiva, R. G., Huitt-Roehl, C. R., Tripathi, A., Cheng, Y. Q., Bosch, J., Townsend, C. A., & Dimopoulos, G. (2018). *Chromobacterium* spp. mediate their anti-Plasmodium activity through secretion of the histone deacetylase inhibitor romidepsin. Scientific reports, 8(1), 6176. (Year: 2018).*

Wang, C., Henkes, L. M., Doughty, L. B., He, M., Wang, D., Meyer-Almes, F. J., & Cheng, Y. Q. (2011). Thailandepsins: bacterial products with potent histone deacetylase inhibitory activities and broad-spectrum antiproliferative activities. Journal of natural products, 74(10), 2031-2038. (Year: 2011).*

Jiang, X. (Ed.). (2019). Sulfur Chemistry. Springer Nature. (Year: 2019).*

Wesener, S. R., Potharla, V. Y., & Cheng, Y. Q. (2011). Reconstitution of the FK228 biosynthetic pathway reveals cross talk between modular polyketide synthases and fatty acid synthase. Applied and environmental microbiology, 77(4), 1501-1507. (Year: 2011).*

Smith, R. C., Reed, V. D., & Hill, W. E. (1994). Oxidation of thiols by copper (II). Phosphorus, Sulfur, and Silicon and the Related Elements, 90(1-4), 147-154. (Year: 1994).*

Hassen, A., Saidi, N., Cherif, M., & Boudabous, A. J. B. T. (1998). Resistance of environmental bacteria to heavy metals. Bioresource technology, 64(1), 7-15. (Year: 1998).*

Benhalima, L., Amri, S., Bensouilah, M., & Ouzrout, R. (2019). Antibacterial effect of copper sulfate against multi-drug resistant nosocomial pathogens isolated from clinical samples. Pakistan Journal of Medical Sciences, 35(5), 1322. (Year: 2019).*

Margolles, A., Mayo, B., & de los Reyes-Gavilán, C. G. (2001). Susceptibility of Listeria monocytogenes and Listeria innocua strains isolated from short-ripened cheeses to some antibiotics and heavy metal salts. Food microbiology, 18(1), 67-73. (Year: 2001).*

Sneath, P. H. A. (1956). Cultural and biochemical characteristics of the genus *Chromobacterium*. Microbiology, 15(1), 70-98. (Year: 1956).*

Collins, M. D., Jones, D., Keddie, R. M., & Sneath, P. H. A. (1980). Reclassification of *Chromobacterium iodinum* (Davis) in a redefined genus *Brevibacterium* (Breed) as *Brevibacterium iodinum* nom. rev .; comb. nov. Microbiology, 120(1), 1-10. (Year: 1980).*

Cheng, Y. Q., Yang, M., & Matter, A. M. (2007). Characterization of a gene cluster responsible for the biosynthesis of anticancer agent FK228 in Chromobacterium violaceum No. 968. Applied and environmental microbiology, 73(11), 3460-3469. (Year: 2007).*

Dall'Agnol, L. T., Martins, R. N., Vallinoto, A. C. R., & Ribeiro, K. T. S. (2008). Diversity of Chromobacterium violaceum isolates from aquatic environments of state of Pará, Brazilian Amazon. Memórias do Instituto Oswaldo Cruz, 103, 678-682. (Year: 2008).*

(Continued)

*Primary Examiner* — Louise W Humphrey
*Assistant Examiner* — Kimberly Breen
(74) *Attorney, Agent, or Firm* — Troutman Pepper Locke LLP (Rochester)

(57) ABSTRACT

The present invention includes a method to increase romidepsin concentration in a bacteria fermentation media. Romidepsin concentration in a fermentation is increased by adding, for example, copper sulfate. The end resulting romidepsin concentration is increased by at least about two fold as compare to fermentation without copper sulfate.

1 Claim, 1 Drawing Sheet

(56) References Cited

OTHER PUBLICATIONS

Dobritsa, A. P., & Samadpour, M. (2019). Reclassification of *Burkholderia insecticola* as *Caballeronia insecticola* comb. nov. and reliability of conserved signature indels as molecular synapomorphies. International journal of systematic and evolutionary microbiology, 69(7), 2057-2063. (Year: 2019).*

Liu, X., Xie, F., Doughty, L. B., Wang, Q., Zhang, L., Liu, X., & Cheng, Y. Q. (2018). Genomics-guided discovery of a new and significantly better source of anticancer natural drug FK228. Synthetic and Systems Biotechnology, 3(4), 268-274. (Year: 2018).*

Arakaki, A.H. et al.; "Optimization of Biomass Production with Copper Bioaccumulation by Yeasts in Submerged Fermentation"; Braz. Arch. Biol. Technol. vol. 54, No. 5, pp. 1027-1034, Sep./Oct. 2011.

International Preliminary Report and Written Opinion dated Jun. 16, 2021, pp. 1-5.

International Search Report and Written Opinion dated Jun. 19, 2020, pp. 1-7.

* cited by examiner

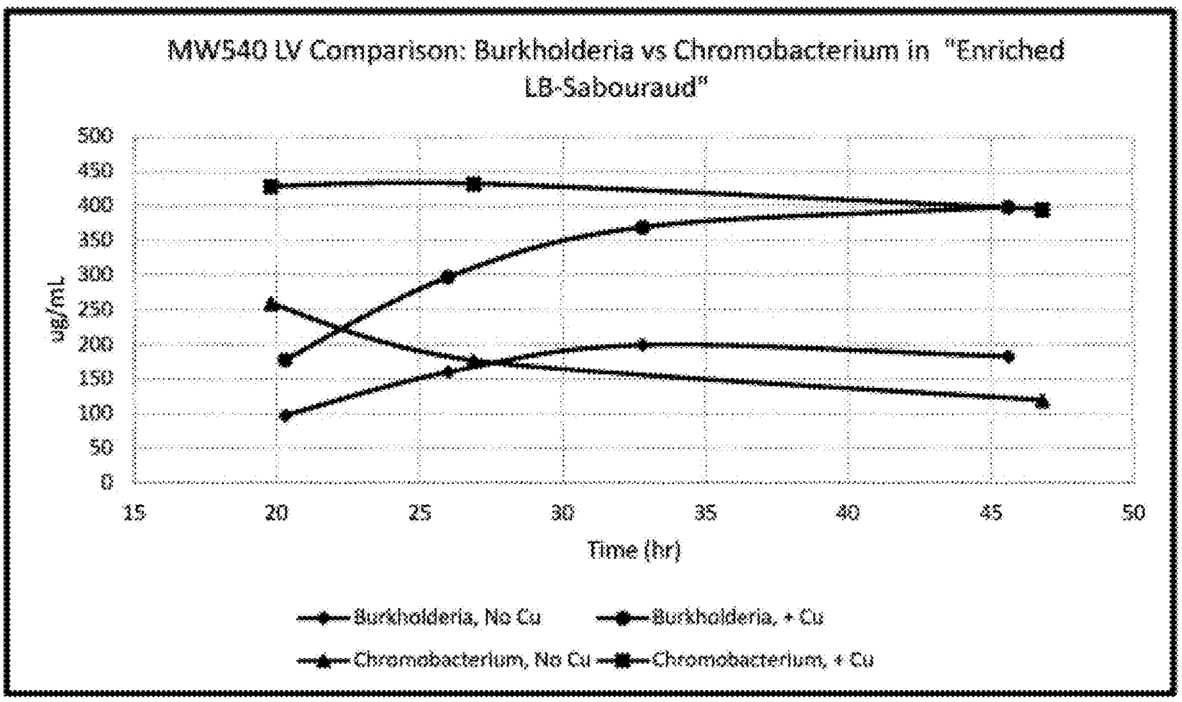
MW540 LV Comparison: Burkholderia vs Chromobacterium in "Enriched LB-Sabouraud"
ug/mL
500
450
400
350
300
250
200
150
100
50
0
15
20
25
30
35
40
45
50
Time (hr)
Burkholderia, No Cu
Burkholderia, + Cu
Chromobacterium, No Cu
Chromobacterium, + Cu

METHOD FOR INCREASING ROMIDEPSIN PRODUCTION FROM FERMENTATION BROTH

This application is a national stage application under 35 U.S.C. § 371 of International Application No. PCT/US2019/058493, filed Oct. 29, 2019, which claims the priority benefit of U.S. Provisional Application Ser. No. 62/904,124 filed Sep. 23, 2019, and U.S. Provisional Application Ser. No. 62/784,656 filed Dec. 24, 2018, which are hereby incorporated by reference in their entirety.

TECHNICAL FIELD OF THE INVENTION

The present invention generally relates to a method for increasing romidepsin production from fermentation broth of a bacterium.

BACKGROUND ART

Without limiting the scope of the invention, its background is described in connection with a method for increasing romidepsin production yield from fermentation broth of bacteria.

Romidepsin, also known as FK228 or FR901228, is a potent histone deacetylase inhibitor. Romidepsin has been shown to have anticancer activities. The drug is approved in the U.S. for treatment of cutaneous T-cell lymphoma (CTCL) and peripheral T-cell lymphoma (PTCL), and is currently being tested, for example, for use in treating patients with other hematological malignancies (e.g, multiple myeloma, etc.) and solid tumors (e.g., prostate cancer, pancreatic cancer, etc.). It is thought to act by selectively inhibiting deacetylases (e.g., histone deacetylase, tubulin deacetylase), promising new targets for development of a new class of anti-cancer therapies. One mode of action involves the inhibition of one or more classes of histone deacetylases (HDAC).

The chemical structure of romidepsin is depicted below as Formula I.

Formula I

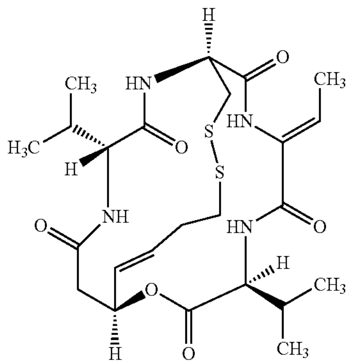

U.S. Pat. No. 4,977,138 describes preparation of romidepsin by culturing microorganism *Chromobacterium violaceum* WB968. Romidepsin is isolated from fermentation broth by extraction and column chromatography.

U.S. Pat. No. 9,701,673 describes romidepsin production by culturing microorganism *Burkholderia* A396.

U.S. Pat. No. 7,396,665 provides an alternative process for the preparation of romidepsin which requires carrying out four column chromatographic purifications steps.

U.S. Pat. No. 8,691,534 describes published processes for the isolation of romidepsin which does not produce pure romidepsin consistently. US'534 patent then goes on to describe an alternative process for the preparation of pure romidepsin to avoid drawbacks of above published processes. US'534 process is carried out at specific pH range and involves use of four chromatographic purifications and two crystallization steps.

A process disclosed in U.S. Pat. No. 4,977,138 for the preparation of romidepsin crystal requires use of three solvents and provides crystals having higher residual solvent content. An improved process described in U.S. Pat. No. 7,611,724 involves use of two solvents which must be used in the specific concentration.

In addition to romidepsin, various derivatives have been prepared and studied. The following patent and patent applications describe various derivatives of romidepsin: U.S. Pat. No. 6,548,479; WO 05/0209134; WO 05/058298; and WO 06/129105; each of which is incorporated herein by reference.

Given the interest in romidepsin as a pharmaceutical agent, there remains a need for preparing large quantities of highly purified material in a cost effective manner. Various reports of purifying romidepsin from fermentation broth have been reported. U.S. Pat. No. 4,977,138; International PCT Application WO 02/20817; each of which is incorporated herein by reference. For example, WO 02/20817 describes increasing the yield of romidepsin from a fermentation process by the addition of specific amino acids such as L-cysteine to the culture medium. Although such discoveries have provided for improved yields of romidepsin by fermentation, there remains a need for better ways of preparing large quantities of pure romidepsin for research and medicinal use.

DISCLOSURE OF THE INVENTION

The present invention, in an aspect, relates to a method of increasing romidepsin concentration in bacteria fermentation comprising the step of adding a di-cationic or bivalent cationic molecule to the fermentation media.

In an aspect, the present invention relates to a method to decrease bacteria fermentation overflow in a bacteria fermentation process. The method includes the step of adding sufficient di-cationic or bivalent cationic molecules to reduce fermentation overflow.

In an aspect, the di-cationic or bivalent cationic molecule of the above embodiments comprise copper (II) sulfate or copper (II) chloride.

In yet another aspect, the bacteria includes *Chromobacterium violaceum* WB968, *Chromobacterium haemolyticum*, or *Burkholderia* A396.

In another aspect, the di-cationic or bivalent cationic molecule concentration comprises at least about two, three, four, five, six, seven, eight, nine, ten, fifty, one hundred, five hundred, one thousand fold or more as compare to trace di-cationic or bivalent cationic molecule originally present in a fermentation media.

Yet in another aspect, the romidepsin concentration from a bacteria fermentation is increased by at least about two, three, four, five, six, seven, eight, nine, tenfold or more.

DESCRIPTION OF THE DRAWINGS

For a more complete understanding of the features and advantages of the present invention, reference is now made to the detailed description of the invention along with the accompanying FIGURES and in which:

The FIGURE denotes the copper effects on the production of FR901228 in *Chromobacterium haemolyticum* and *Burkholderia rinojensis* fermentation.

DESCRIPTION OF EMBODIMENTS

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used herein, the term "romidepsin", "FK228", "FR901228", "NSC630176", or "depsipeptide" are used interchangeably and refer to the compound of Formula I.

The term "isolation of romidepsin" refers to a process of separating romidepsin from the fermentation broth of bacteria. In general, isolation includes one or more steps selected from extraction, chromatography and/or crystallization.

The term "fermentation broth" or "whole cell broth" refers to the broth obtained by culturing a microorganism capable of producing romidepsin, for example *Chromobacterium violaceum* or *Burkholderia* A396. The fermentation broth can be prepared by the process described in the art, for example U.S. Pat. Nos. 4,977,138 and/or 9,701,673. All of which are incorporated herein by reference in their entirety.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, "di-cationic" or "bi-valent cationic" molecule means any molecule that has two positive charges. For example, copper (II) sulfate or copper (II) chloride.

Bacteria Fermentation

*Chromobacterium violaceum* WB968 or *Burkholderia* A396 are non-limiting examples of bacteria known in the art to produce romidepsin by fermentation. Any bacteria can be used for the present invention, as long as romidepsin is produced.

For fermentation, typically, the carbon source in the culture medium can be any carbohydrate. In certain embodiments, the carbon source is a monosaccharide or disaccharide (e.g., glucose). In certain particular embodiments, the carbon source is glucose or maltodextrin. Other carbohydrates such as starch, maltose, sucrose, fructose, or glycerin may be used in certain embodiments. In certain embodiments, the source of some or all of the carbon can also be an amino acid or complex nutrient that provides carbon and some or all of the nitrogen. In certain embodiments, the nitrogen source is ammonia or an ammonium salt such as ammonium sulfate, ammonium nitrate, ammonium phosphate, etc. In other embodiments, nitrogen and some or all of the carbon come from plant peptone (e.g., polypeptone NS, corn steep liquor, Hinute R). Other complex sources of nitrogen and carbon that may be used include bouillon, yeast extract, soy peptone, gluten meal, cotton seed flour, soybean meal, dried yeast, and wheat germ. In certain embodiments, the nitrogen source is urea or amino acids. In certain embodiments, the nitrogen source is an organic small molecule containing nitrogen. In certain embodiments, the medium is supplemented with amino acids. For example, the medium may be supplemented with L-arginine, L-histidine, or L-cysteine. In certain embodiments, the medium is supplemented with L-cysteine. See WO 02/20817; incorporated herein by reference in its entirety. In certain embodiments, the medium is supplemented with L-cysteine and L-valine. Such supplementation is thought to increase the amount of romidepsin produced in the fermentation and/or reduce the amount of related substances and/or degradants. The culture medium may include minerals such as magnesium (e.g., magnesium sulfate), and phosphate (e.g., potassium dihydrogenphosphate, disodium hydrogenphosphate). In certain embodiments, the culture medium includes glucose, plant peptone (polypeptone NS) or corn steep liquor (CSL), magnesium sulfate, and water. In certain embodiments, the culture medium includes glucose, polypeptone (polypeptone NS), magnesium sulfate, an antifoaming agent, and water. In certain embodiments, the culture medium includes glucose (0.45-1.0%), plant peptone (polypeptone NS) or CSL (0.9-4.0%), magnesium sulfate (0.0054-0.010%), an antifoaming agent (0.09%-0.11%), and water (balance). In certain embodiments, the culture medium includes glucose, oxidized starch (e.g., Pinedex #100) or maltodextrin, soy peptone (e.g., Hinute-R), ammonium sulfate, magnesium sulfate, potassium dihydrogenphosphate, disodium hydrogen phosphate, anti-foaming agent (e.g., Adekanol LG-109), L-cysteine, L-valine, and water. In certain embodiments, the culture medium includes glucose (2-10%), oxidized starch (e.g., Pinedex #100) or maltodextrin (1-15%), soy peptone (e.g., Hinute-R) (1-6%), ammonium sulfate (0-0.5%), magnesium sulfate (0-2%), potassium dihydrogenphosphate (0.275-1.65%), disodium hydrogen phosphate (0.18-1.08%), anti-foaming agent (e.g., Adekanol LG-109) (0.2-0.66%), L-cysteine (0-30 mM), L-valine (0-15 mM), and water.

The culture is typically grown under conditions (e.g., temperature, pH, oxygen concentration, etc.) suitable for growth of the organism. In certain embodiments, the pH of the culture is monitored and/or adjusted. The pH of the culture may range from a pH of 3.0 to 7.5. Any organism for romidepsin production will have a preferred temperature for growth depending on the conditions under which the culture is grown. In certain embodiments, the culture is grown at a temperature ranging from 15° C. to 39° C. In certain embodiments, the culture is grown at a temperature between 18° C. to 27° C. In certain embodiments, the culture is grown at a temperature of approximately 18° C. In certain embodiments, the culture is grown at a temperature of approximately 19° C. In certain embodiments, the culture is grown at a temperature of approximately 20° C. In certain embodiments, the culture is grown at a temperature of approximately 21° C. In certain embodiments, the culture is grown at a temperature of approximately 22° C. In certain embodiments, the culture is grown at a temperature of approximately 23° C. In certain embodiments, the culture is grown at a temperature of approximately 24° C. In certain embodiments, the culture is grown at a temperature of approximately 25° C. In certain embodiments, the culture is grown at a temperature of approximately 26° C. In certain embodiments, the culture is grown at a temperature of approximately 27° C. In certain embodiments, the culture is grown at a temperature of approximately 28° C. In certain embodiments, the culture is grown at a temperature of approximately 29° C. In certain embodiments, the culture is grown at a temperature of approximately 30° C. In certain embodiments, the culture is grown at a temperature of approximately 31° C. In certain embodiments, the culture is grown at a temperature of approximately 32° C. In certain embodiments, the culture is grown at a temperature of approximately 33° C. In certain embodiments, the culture is grown at a temperature of approximately 34° C. In certain embodiments, the culture is grown at a temperature of approximately 35° C. In certain embodiments, the culture is grown at a temperature of approximately 36° C. In certain embodiments, the culture is grown at a temperature of approximately 37° C. In certain embodiments, the culture is grown at a temperature of approximately 38° C. In certain embodiments, the culture is grown at a temperature of approximately 39° C.

The oxygen concentration in the culture is maintained at a level greater than 0%. In certain embodiments, the oxygen concentration is maintained above 20%. The oxygen level is maintained by aeration, pressure, and/or agitation.

The resulting culture is typically grown for approximately 10-100 hours. The culture may be harvested after 20, 30, 40, 50, 60, 70, or 80 hours. In certain embodiments, the culture is harvested after approximately 30, 35, 40, 45, or 50 hours. In certain embodiments, the culture is harvested at approximately 36 hours. In certain embodiments, the culture is harvested at approximately 50 hours. Typically, the culture is grown until saturation. Since romidepsin can be a secondary metabolite, yields can be derived from later stage cultures. In some embodiments, the culture can be harvested in log phase. As would be appreciated by one of skill in the art, the culture can be typically harvested before significant amounts of degradants are formed. The harvest time can be determined empirically by assaying sample of the fermentation for the production of romidepsin. In certain embodiments, the culture is harvested when the titer of romidepsin reaches between 0.1 and 2.0 g/kg. In certain embodiments, the culture is harvested when the titer reaches at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 g/kg. In certain embodiments, the culture is harvested when the titer reaches at least 0.8 g/kg. The sample can also be assayed for related substances or degradants, and the culture harvested when a desired level of romidepsin, desired level of related substances or degradants, or a ratio of the two is achieved. The time of harvesting can also be determined based on the consumption of a component in the media such as glucose. In other embodiments, the time of harvesting can be based on the production of a metabolite. The time of harvesting can be determined based on a combination of the above criteria.

After the culture is grown for a sufficient amount of time, the culture is harvested. The desired romidepsin can be found in the culture medium as well as in the cells of the culture. The cells are optionally killed and/or lysed before purification. In certain embodiments, the cells are killed with the addition of chemicals such as sulfuric acid, or by adding heat.

Addition of Di-Cationic or Bivalent Cationic Molecule.

In one embodiment, di-cationic molecule, in the form of copper (II) sulfate, can be added at the beginning, during or near the end of the fermentation process of bacteria fermentation such as *Chromobacterium violaceum* WB968 or *Burkholderia* A396. Most fermentation media contain trace amount of di-cationic or bivalent cationic molecule such as copper sulfate. In certain embodiments, the di-cationic or bivalent cationic molecule concentration comprises at least about two, three, four, five, six, seven, eight, nine, ten, fifty, one hundred, five hundred, one thousand fold or more as compare to trace di-cationic or bivalent cationic molecule originally present in a fermentation media.

Purification

The resulting material can then optionally be reduced in volume. The romidepsin can be purified by any purification techniques known in the art for purifying peptides, natural products, and/or organic molecules. Exemplary purification techniques include batch chromatography, column chromatography, solvent extraction, and crystallization. The purification process can include one or more steps in order to achieve the desired degree of purity. In certain embodiments, the extracted material is purified using a non-ionic adsorption resin. In certain embodiments, a reverse phase resin is used in the fractionation step. In certain particular embodiments, multiple column chromatography steps using a reverse phase resin are used. Exemplary resins useful in the purification process include alumina, silica gel, SEPABEADS SP850, DIAION HP20SS, and DIAION HP20. In certain embodiments, the DIAION HP20SS resin and/or DIAION HP20 resin is obtained from Mitsubishi Chemical Corporation. In certain embodiments, alumina is used as the column material. In certain embodiments, silica gel is used as the resin.

The purity of the romidepsin can be assessed using any method known in the art. Methods of assessing purity include appearance, HPLC, specific rotation, NMR spectroscopy, IR spectroscopy, UV/Visible spectroscopy, powder x-ray diffraction (XRPD) analysis, elemental analysis, LC-mass spectroscopy, and mass spectroscopy. In certain embodiments, the purity is assessed by HPLC, which has detection limit for impurities of approximately 0.05%. In certain embodiments, the purity is assessed by NMR spectroscopy. In certain embodiments, the purity is assessed by IR spectroscopy. In certain embodiments, the purity is assessed by UV/Visible spectroscopy. In certain embodiments, the purity is assessed by XRPD.

In an embodiment, the addition of bivalent or di-cationic molecule surprisingly increases the production of romidepsin (yield) by at least about 2 fold, 3 fold, 4 fold, 5 fold, 6 fold, 7 fold, 8 fold, 9 fold, and/or 10 fold.

EXAMPLES

Example 1

Copper sulfate is added to the fermentation media of *Burkholderia* A396, to reach the final concentration of about 1250 micromolar. A side by side comparison was made to compare to standard *Burkholderia* A396 fermentation with only trace amount copper sulfate in standard fermentation media. After fermentation, the secondary metabolites are purified and analyzed for the presence of romidepsin. The end results are shown to have improved amount of romidepsin production by at least about two fold with about 1250 micromolar of copper sulfate as compare to trace amount of copper sulfate.

Example 2

Copper sulfate is added to the fermentation media of *Chromobacterium violaceum* WB968, as compare to standard *Chromobacterium violaceum* WB968 fermentation with trace amount of copper sulfate. After fermentation, the secondary metabolites are purified and analyzed for the presence of romidepsin. The end results are shown to have improved amount of romidepsin production by at least about two fold when copper sulfate is added.

Example 3

For this example, *Chromobacterium haemolyticum* and *Burkholderia rinojensis* working cell bank stocks were generated with LB-Lennox media and 10% glycerol. The LB-Lennox media was made at a lower pH (5.50) to accommodate more growth for highly viable working cell banks. This medium also served as the seed flask for growing the inoculum for fermentor testing. LB-Lennox media content is as follows:

| LB-Lennox Components | (g/L) |
|---|---|
| Casein Tryptone | 10.0 |
| Yeast Extract | 5.0 |
| Sodium Chloride | 5.0 |
| pH adjusted to 5.50 with 11N Phosphoric Acid or 10N Sodium Hydroxide | |

Throughout development, several media options stood out for the production fermentor, however only a select few options actually made it to larger scale fermentor testing (5 Liter working volume). One of these options, a modified medium that was a blend of several different common media designs, proved to be successful with both microbes. The media design is listed below:

| E-LB-Sabouraud Components | (g/L) |
|---|---|
| Dextrose Monohydrate (Added Post-Sterilization) | 44.0 |
| Casein Tryptone | 10.0 |
| Yeast Extract | 5.0 |
| Potassium Phosphate Dibasic | 7.5 |
| Potassium Phosphate Monobasic | 5.0 |
| Monosodium Glutamate Monohydrate | 5.0 |
| L-Cysteine | 0.5 |
| Copper Sulfate Anhydrous (Added Post-Sterilization to appropriate fermentors). | 0.1 |
| pH controlled at 5.50 +/− 0.05 with 11N Phosphoric Acid and 7.4N Ammonium Hydroxide | |

This medium was inoculated at 1% v/v with the seed flask of each microbe and the fermentations were ran until glucose exhaustion (or halting of consumption) and then ran for a further day, up until about 46 hours, to observe the Romidepsin trend. Copper Sulfate was only added to the treatment tanks, while the controls did not receive copper. The resulting data is depicted in The FIGURE.

In The FIGURE, for both microbes, the copper treatment had the soluble Romidepsin concentration stabilize at about 400 mg/L. The non-copper fermentations however, peaked at around 200-250 mg/L, and dropped with further fermentation time. Both *Chromobacterium* tanks were finished growing by ~27 hours, while both *Burkholderia* tanks were done growing at ~33 hours.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of increasing romidepsin concentration in a bacterial fermentation comprising:

fermenting a *Chromobacterium haemolyticum* or *Burkholderia rinojensis* bacterial strain in a fermentation medium comprising 0.1 g/L copper (II) sulfate, wherein said copper (II) sulfate increases romidepsin production compared to a fermentation that is identical but without the copper (II) sulfate in the medium.

* * * * *